United States Patent
O'Phelan et al.

(10) Patent No.: US 6,522,525 B1
(45) Date of Patent: Feb. 18, 2003

(54) IMPLANTABLE HEART MONITORS HAVING FLAT CAPACITORS WITH CURVED PROFILES

(75) Inventors: Michael J. O'Phelan, Oakdale, MN (US); Brian L. Schmidt, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/705,976

(22) Filed: Nov. 3, 2000

(51) Int. Cl.$^7$ .......................... H01G 9/045; H01G 9/10; A61N 1/40

(52) U.S. Cl. .......................... 361/509; 361/519; 607/5

(58) Field of Search .................. 361/503–520; 607/5

(56) References Cited

U.S. PATENT DOCUMENTS

| | | | |
|---|---|---|---|
| 3,643,168 A | 2/1972 | Manicki | 325/459 |
| 3,723,926 A | 3/1973 | Thomas et al. | 335/268 |
| 3,777,570 A | 12/1973 | Thomas et al. | 73/398 |
| 3,826,143 A | 7/1974 | Thomas et al. | 73/398 C |
| 3,859,574 A | 1/1975 | Brazier | 317/230 |
| 4,047,790 A | 9/1977 | Carino | 339/220 |
| 4,086,148 A | 4/1978 | Badia | 204/33 |
| 4,088,108 A | 5/1978 | Hager | 123/148 CC |
| 4,131,935 A | 12/1978 | Clement | 361/433 |
| 4,782,340 A | 11/1988 | Czubatyj et al. | 340/825.83 |
| 5,131,388 A | 7/1992 | Pless et al. | 128/419 D |
| 5,439,760 A | 8/1995 | Howard et al. | 429/94 |
| 5,471,087 A | 11/1995 | Buerger, Jr. | 257/532 |
| 5,522,851 A | 6/1996 | Fayram | 607/5 |
| 5,527,346 A | 6/1996 | Kroll | 607/5 |
| 5,584,890 A | 12/1996 | MacFarlane et al. | 29/25.03 |
| 5,628,801 A | 5/1997 | MacFarlane et al. | 29/25.03 |
| 5,658,319 A | 8/1997 | Kroll | 607/7 |
| 5,716,729 A | 2/1998 | Sunderland et al. | 429/66 |
| 5,779,891 A | 7/1998 | Andelman | 210/198.2 |
| 5,801,917 A | 9/1998 | Elias | 361/535 |
| 5,814,082 A | 9/1998 | Fayram et al. | 607/5 |
| 5,867,363 A | 2/1999 | Tsai et al. | 361/502 |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |
| 5,930,109 A | 7/1999 | Fishler | 361/508 |
| 5,963,418 A | 10/1999 | Greenwood, Jr. et al. | 361/508 |
| 5,968,210 A | 10/1999 | Strange et al. | 29/25.03 |
| 5,983,472 A | 11/1999 | Fayram et al. | 29/25.42 |
| 6,006,133 A | 12/1999 | Lessar et al. | 607/5 |
| 6,009,348 A | 12/1999 | Rorvick et al. | 607/5 |
| 6,032,075 A | 2/2000 | Pignato et al. | 605/5 |
| 6,042,624 A | 3/2000 | Breyen et al. | 29/25.03 |
| 6,094,788 A | 8/2000 | Farahmandi et al. | 25/24.41 |

(List continued on next page.)

Primary Examiner—Dean A. Reichard
Assistant Examiner—Eric W. Thomas
(74) Attorney, Agent, or Firm—Schwegman, Lundberg, Woessner & Kluth, P.A.

(57) ABSTRACT

Implantable heart-monitoring devices, such as defibrillators, pacemakers, and cardioverters, detect onset of abnormal heart rhythms and automatically apply corrective electrical therapy, specifically one or more bursts of electric charge, to abnormally beating hearts. Critical parts in these devices include the capacitors that store and deliver the bursts of electric charge. Some devices use flat aluminum electrolytic capacitors have cases with right-angle corners which leave gaps when placed against the rounded interior surfaces of typical device housings. These gaps and voids not only waste space, but ultimately force patients to endure implantable devices with larger housings than otherwise necessary. Accordingly, the inventors devised several capacitor structures that have curved profiles conforming to the rounded interior surfaces of device housings. Some exemplary capacitor embodiments include two or more staggered capacitor elements, and other embodiments stagger capacitors of different types and/or sizes.

27 Claims, 7 Drawing Sheets

U.S. PATENT DOCUMENTS

| | | |
|---|---|---|
| 6,099,600 A | 8/2000 | Yan et al. .................. 29/25.03 |
| 6,110,233 A | 8/2000 | O'Phelan et al. .......... 29/25.03 |
| 6,118,651 A | 9/2000 | Mehrotra et al. ........... 361/509 |
| 6,141,205 A | 10/2000 | Nutzman et al. ........... 361/509 |
| 6,157,531 A | 12/2000 | Breyen et al. .............. 361/519 |
| 6,184,160 B1 | 2/2001 | Yan et al. ................... 438/800 |
| 6,191,931 B1 | 2/2001 | Paspa et al. ................ 361/302 |
| 6,212,063 B1 | 4/2001 | Johnson et al. ............. 361/517 |
| 6,297,943 B1 | 10/2001 | Carson ....................... 361/500 |
| 6,299,752 B1 | 10/2001 | Strange et al. .............. 205/152 |
| 6,321,114 B1 | 11/2001 | Nutzman et al. .............. 607/5 |

IMPLANTABLE HEART MONITORS HAVING FLAT CAPACITORS WITH CURVED PROFILES

CROSS-REFERENCE TO RELATED APPLICATIONS

This application is related to application Ser. No. 09/706,447, filed on Nov. 3, 2000, entitled FLAT CAPACITOR FOR AN IMPLANTABLE MEDICAL DEVICE, which is incorporated herein by reference in its entirety.

TECHNICAL FIELD

This invention relates generally to electrolytic capacitors and, more particularly to flat electrolytic capacitors for use in implantable heart monitors.

BACKGROUND OF THE INVENTION

Since the early 1980s, thousands of patients prone to irregular and sometimes life threatening heart rhythms have had miniature heart-monitoring devices, such as defibrillators, pacemakers, and cardioverters, implanted in their bodies. These devices detect onset of abnormal heart rhythms and automatically apply corrective electrical therapy, specifically one or more bursts of electric current, to their hearts. When the bursts of electric current are properly sized and timed, they restore normal heart function without human intervention, sparing patients considerable discomfort and often saving their lives.

The typical implantable heart-monitoring device includes a set of electrical leads, which extend from a sealed housing for implantation into the inner walls of a heart. The housing itself is typically somewhat flat and rectangular with rounded edges and corners to reduce stress on surrounding tissues after implantation. Within the housing are a battery for supplying power, heart-monitoring circuitry for monitoring the heart and detecting abnormal rhythmic conditions, and two or more capacitors for delivering bursts of electric current through the leads to the heart.

In many instances, each capacitor takes the form of a flat aluminum electrolytic capacitor. This type of capacitor generally includes a vertical stack of several flat D-shaped capacitor elements, or modules, with each module comprising at least one D-shaped paper separator sandwiched between D-shaped sheets of aluminum foil. The capacitor modules are electrically coupled together to provide a total capacitance and then housed in a D-shaped case made of aluminum or another metal compatible with the foil.

The aluminum case, which conforms closely to the shape of the vertical stack of D-shaped capacitor modules, has vertical sidewalls that are parallel to the vertical faces of the stack. The case also has D-shaped top and bottom portions that meet its vertical sidewalls to form approximate right-angle joints and corners along its top and bottom edges.

Two or more such capacitors are sometimes stacked on top of each other within the housing of an implantable device. When stacked, the walls of the D-shaped capacitors are aligned with each other, effectively forming a single vertical wall the combined height of the capacitors.

One problem with these types of flat capacitors and their stacked arrangement in implantable device housings is that the walls of the cases are incompatible with the rounded edges and corners of implantable device housings. Juxtaposing these vertical walls and right-angle corners against the rounded interior portions of the housings inevitably leaves gaps or voids between the cases and housings. These voids not only waste space, but ultimately force patients to endure implantable devices with larger housings than otherwise necessary.

Accordingly, there is a need for flat capacitors that better conform to the rounded portions of implantable medical-device housings.

SUMMARY

To address this and other needs, the inventors devised new capacitor structures, new capacitor shapes, and new capacitor assemblies to conform better with the housings of implantable medical devices. One exemplary capacitor includes three or more capacitive modules that are sized and stacked so that their edges on at least one side are staggered relative each other in one or two dimensions to define a curved profile that conforms generally with a rounded, interior surface of a capacitor case.

The inventors also devised new capacitor shapes, some of which incorporate one or more rounded corners. One exemplary capacitor includes a main portion and two peninsular portions extending from one side of the main portion, defining a "U." Terminals extend from the end of one of the peninsular portions. One innovative use of this shape entails placing a battery or other component of an implantable medical device in the region between the two peninsular portions.

Additionally, the inventors devised new capacitor assemblies. One exemplary capacitor assembly includes two or more separate capacitors of different sizes. In some embodiments, one or more of these capacitors include a curved profile and/or are staggered relative each other. In other embodiments, two or more capacitors of the same size are staggered relative each other.

Other aspects of the invention include an implantable medical device, such as a pacemaker, defibrillator, cardioverter-defibrillator, or congestive-heart-failure device, that has a housing with at least one rounded surface abutting the rounded portion of a capacitor. The capacitor includes a capacitive stack with a curved profile and/or includes a pair of peninsular portions spaced to receive a battery or other component. Other implantable devices include one or more of the new capacitive assemblies.

DETAILED DESCRIPTION OF THE EMBODIMENTS

The following detailed description, which references and incorporates the above-identified figures, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

As used herein, the term "profile" refers to the general outline of a portion of an object taken in or projected onto a plane generally perpendicular to a major surface of the object. Thus, for example, in some flat capacitors, profile means the outline of the capacitor case and/or the capacitor stack taken in a plane perpendicular to the major surfaces of the case or the capacitor stack.

As used herein, the term "staggered" refers to the existence of an offset between respective adjacent surfaces of two or more juxtaposed or proximate objects. Thus, for example, the offset can result from offsetting one of the objects relative the other object or controlling the relative size and placement of the objects.

Figure 1:
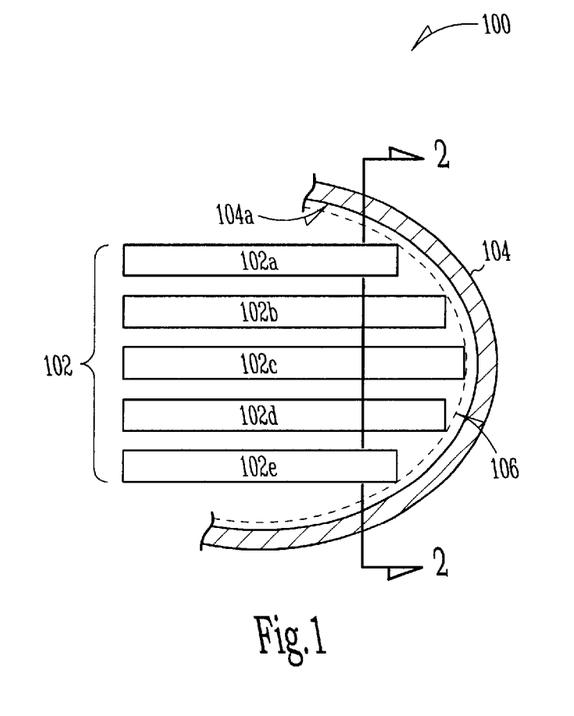
FIG. 1 is a partial cross-sectional view of an exemplary capacitor 100 having capacitor modules with edges staggered in a first dimension to define a curved profile 106.

FIG. 1 shows a portion of an exemplary capacitor 100 incorporating the present invention. Capacitor 100 includes a stack 102 of two or more electrically coupled capacitor modules 102a, 102b, 102c, 102d, and 102e within a capacitor case 104. Modules 102a–102e are staggered so that their edges generally (or at least a portion of side of the stack) define a profile 106 that generally conforms or is substantially congruent to an adjacent curved interior portion 104a of capacitor case 104.

Figure 2:
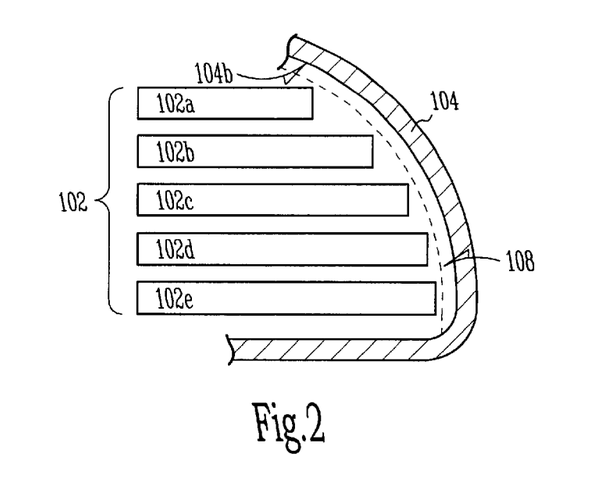
FIG. 2 is a partial cross-sectional view of capacitor 100 showing that its capacitor modules are staggered in a second dimension to define another curved profile 108.

FIG. 2, a section view of capacitor 100 taken along line 2—2, shows that modules 102a–102e are staggered in two dimensions. In this view, capacitor modules 102a–102e define a profile 108, which is generally congruent to a curved portion 104b of case 104. Although profiles 106 and 108 are quite distinct in this exemplary embodiment, other embodiments make profiles 106 and 108 substantially congruent.

In the exemplary embodiment, each capacitor module includes a three-layer etched and/or perforated anode, a cathode, and at least one electrolyte-carrying separator between the anode and the cathode. The anode and cathode comprise foils of aluminum, tantalum, hafnium, niobium, titanium, zirconium, or combinations of these metals. Additionally, each capacitor module is sandwiched between two pairs of electrolyte-carrying separators, with the separators extending beyond the anode and cathode to prevent undesirable shorting with the case. Alternatively, separate insulative layer can be placed between the capacitor modules and the case interior walls to prevent shorting. Exemplary separators comprise kraft paper, and exemplary electrolytes include ethylene-glycol base combined with butrylactone.

In other embodiments, the capacitor modules take other forms having different numbers of anode layers and separators. For example, in some embodiments, the anodes, cathode, and separators in one or more of the capacitor modules are staggered to define curved module faces that confront the interior surfaces 104a or 104b of the case. Also, in some embodiments, one or more of the anodes or cathodes are coupled to the case, making it either anodic or cathodic.

To define the staggered edge faces and thus the curved profile, some embodiments which provide the curved profile in a single dimension, use a set of generally congruent modules of different sizes. For example, one embodiment includes four generally D-shaped modules, each with a common width and height, but with four successively smaller lengths. The modules are stacked, each module having at least one edge aligned vertically with the corresponding edges of adjacent modules.

Figure 3:
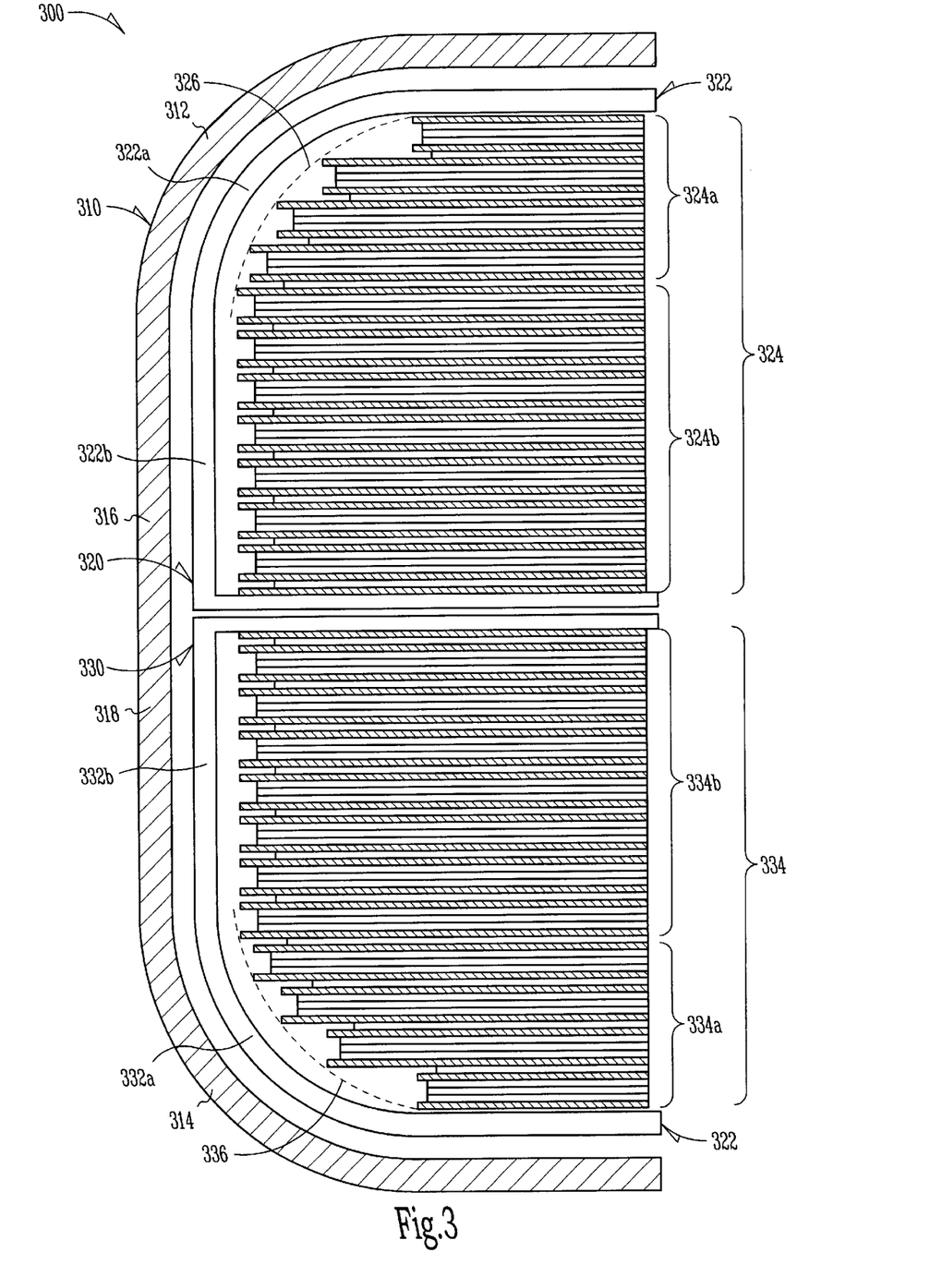
FIG. 3 is a partial cross-sectional view of an exemplary implantable heart monitor 300 including a monitor housing 310 and two capacitors 320 and 330 having curved profiles that abut interior curved portions of the monitor housing.

FIG. 3 shows an exemplary implantable heart monitor 300 including a monitor housing 310 and two capacitors 320 and 330. Monitor housing 310 includes curved portions 312 and 314 and adjoining straight portions 316 and 318. Capacitor 320 includes case 322 and eleven capacitor modules 324. Case 322 includes a curved portion 322a and a straight portion 322b, respectively confronting curved portion 312 and straight portion 316 of housing 310.

Capacitor modules 324 include a set of staggered modules 324a and a set of unstaggered modules 324b. The set of staggered modules 324a confront curved portion 322a of case 322 and have edges arranged to define a curved profile 326 generally congruent to the profile of curved portion 322. Modules 324b, which are vertically aligned, confront straight portion 322b of case 322.

Similarly, capacitor 330 includes case 332 and eleven capacitor modules 334. Case 332 includes curved portion 332a and a straight portion 332b, which confront respective portion 314 and 318 of housing 310. Capacitor modules 334 include staggered modules 334a, which confront curved portion 332a of case 332, have front edges arranged to define a curved profile 336 generally congruent to the profile of curved portion 332a. Modules 334b confront straight portion 332b of case 332.

Notably, the exemplary embodiment provides each of modules 324 and 334 with three anodes placed between one or more separators and at least one cathode placed adjacent one of the separators. (FIG. 3 shows the separators cross-hatched.) However, the invention is not limited to any particular module arrangement. Indeed, some embodiments of the invention use other (greater or lesser) numbers of anodes as well as modules. Moreover, some embodiments mix modules of different arrangements within the same capacitor case. This allows greater flexibility in exploiting the space available in the case as well as the housing.

Additionally, other embodiments of the invention construct capacitor cases 322 and 332 as a single case having two adjacent compartments with a common wall. Modules 324 and 334 are each placed in a respective compartment. The cathodes in modules 324 and the anodes of modules 334 are electrically coupled to the case; an external anode terminal is coupled to the anodes of module 324; and an external cathode terminal is coupled to the cathodes of module 334, thereby effecting a series connection of the two capacitors using two external terminals instead of the four that are conventionally provided.

This arrangement can be made by providing two (first and second) aluminum case bodies having the desired curved portions, placing capacitor modules in the first case body, and welding a cover to the first case body. Other capacitor modules can then be stacked and placed in the second case body. The cover of the first case body is then put on the opening of the second case body and welded in place.

Figure 4:
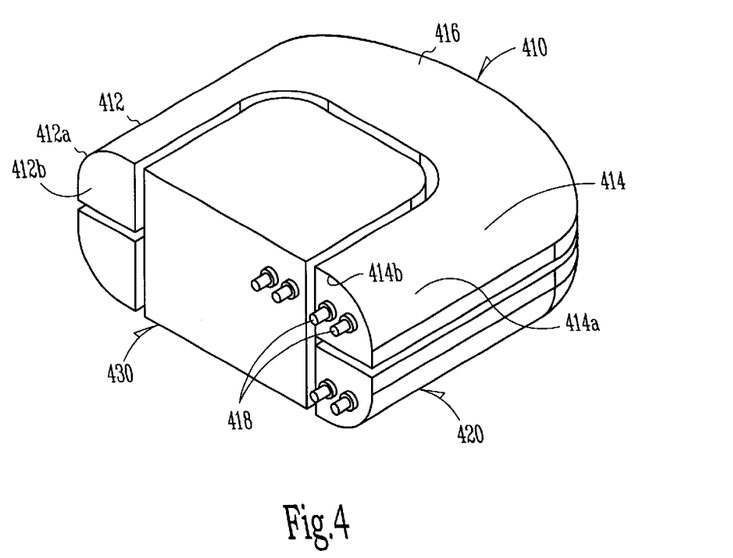
FIG. 4 is a perspective view of an exemplary capacitor-battery assembly 400 including two stacked U-shaped capacitors 410 and 420 and a battery 430 nested within the capacitors.

FIG. 4 shows a perspective view of an exemplary capacitor-battery assembly 400 including two stacked U-shaped capacitors 410 and 420 and a battery 430 nested within the capacitors. For sake of brevity, capacitor 420, which is of substantially identical size, shape, and structure as capacitor 410 in this exemplary assembly, is not described separately. However, the invention is not so limited. Capacitor 410 includes legs 412 and 414, respective middle (or intermediate) portions 416, and terminals 418. Legs 412 and 414, which are parallel in the exemplary embodiment, include respective curved surfaces 412a and 414a, and respective flat end surfaces 412b and 414b.

Figure 5:
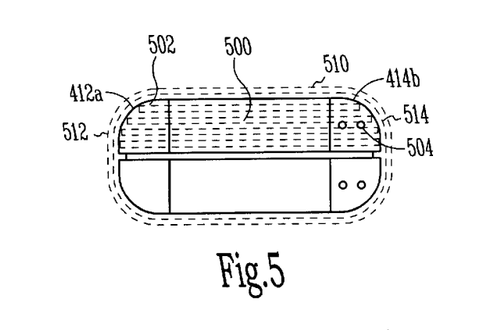
FIG. 5 is a front view of the FIG. 4 assembly without the battery.

FIG. 5, a front view of assembly 400 without battery 430, shows that curved surfaces 412a and 414b are generally congruent to each other and to respective curved profile 502 and 504 defined by capacitor modules 500. Further, it shows a housing 510 (in phantom) having a curved or concave portions 512 and 514 generally congruent with or conformant to curved (or convex) surfaces 412a and 414a. In the exemplary embodiment, curved profiles 502 and 504 are quarter segments of an ellipse or circle, and surfaces 412a and 414a are portions of an ellipsoid or sphere. The exemplary embodiment provides the modules with one or more of the single or multiple anode structures noted previously. Thus, modules 500 may include modules with differing anode structures as desired to fit a given height.

Figure 6:
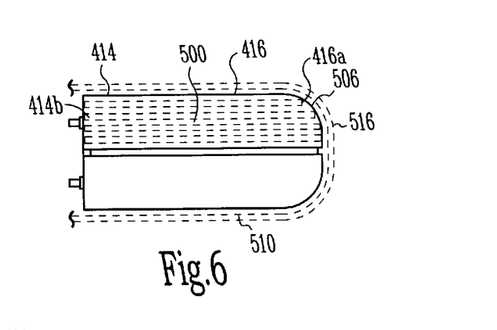
FIG. 6 is a side view of the FIG. 4 assembly.

FIG. 6, a side view of assembly 400, shows that the curved surfaces 412a and 414a are generally perpendicular to end surfaces 412a and 412b. Middle portion 416 is also shown as having a curved portion 416a which is congruent to a curved profile 506 defined by capacitor modules 500 and a curved portion 516 of monitor housing 510.

Figure 7:
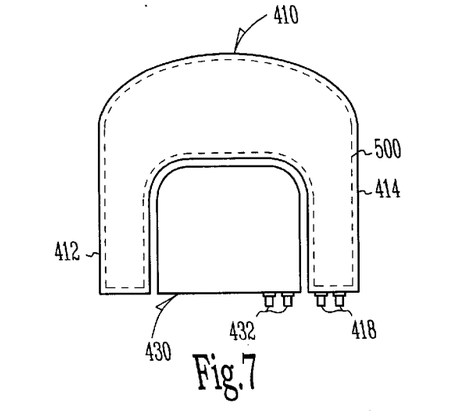
FIG. 7 is a top view of the FIG. 4 assembly.

FIG. 7 is a top view of assembly 400, showing the general U-shape of capacitor modules 500. This figure also shows that battery 430 includes terminals 432.

Figure 8:
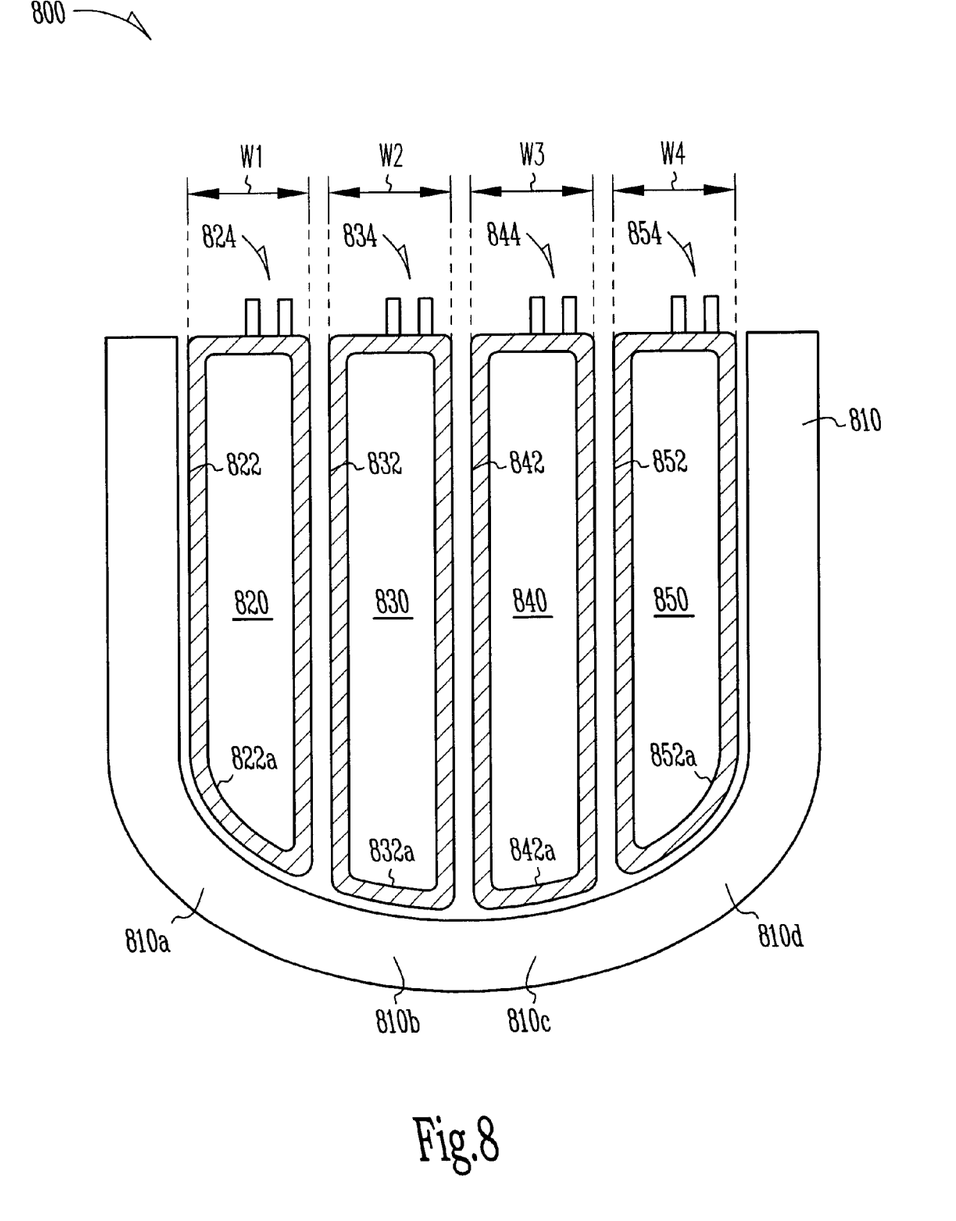
FIG. 8 is a partial cross-sectional view of an exemplary capacitor assembly 800.
Figure 9:
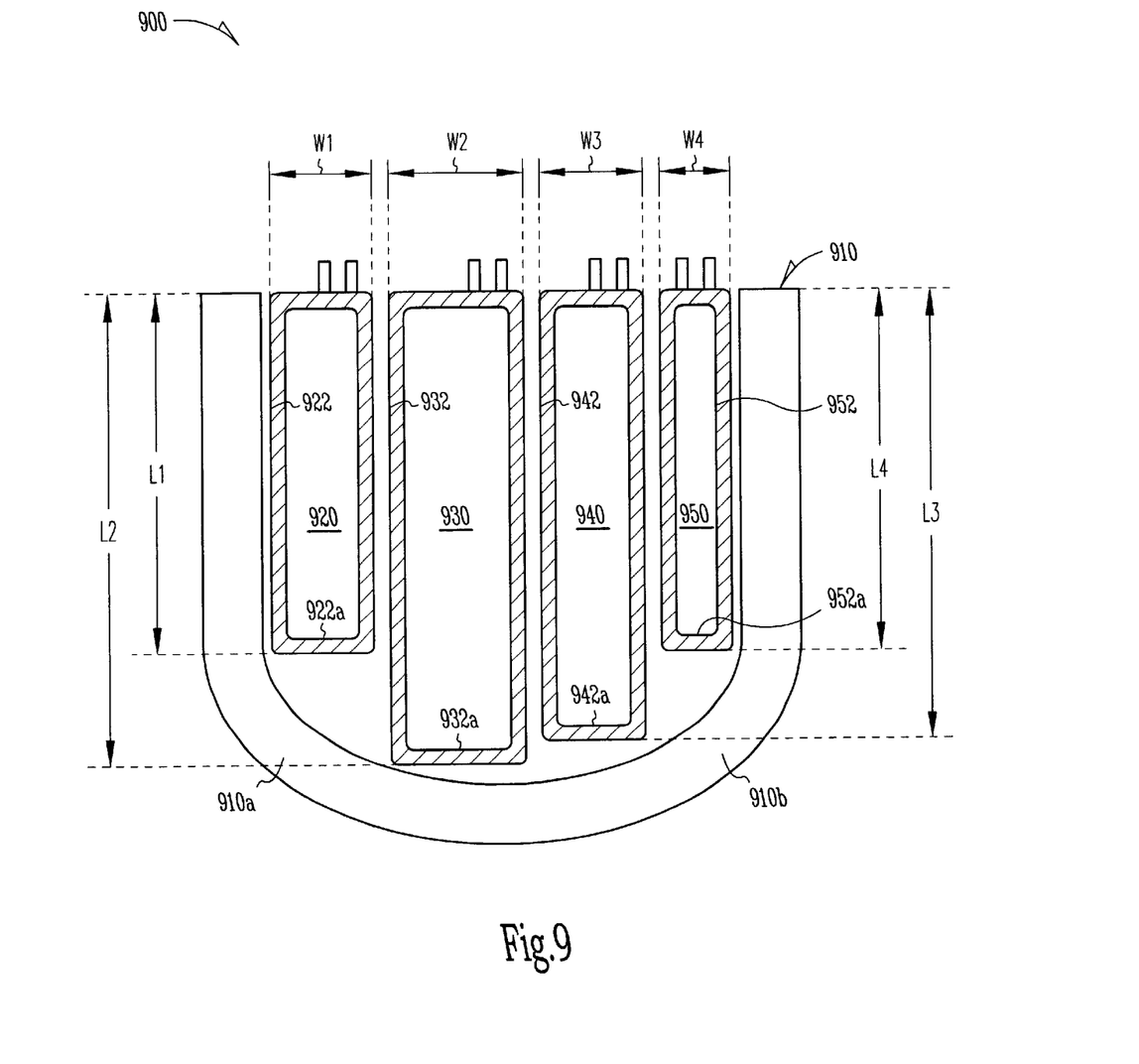
FIG. 9 is a partial cross-sectional view of an exemplary capacitor assembly 900.
Figure 10:
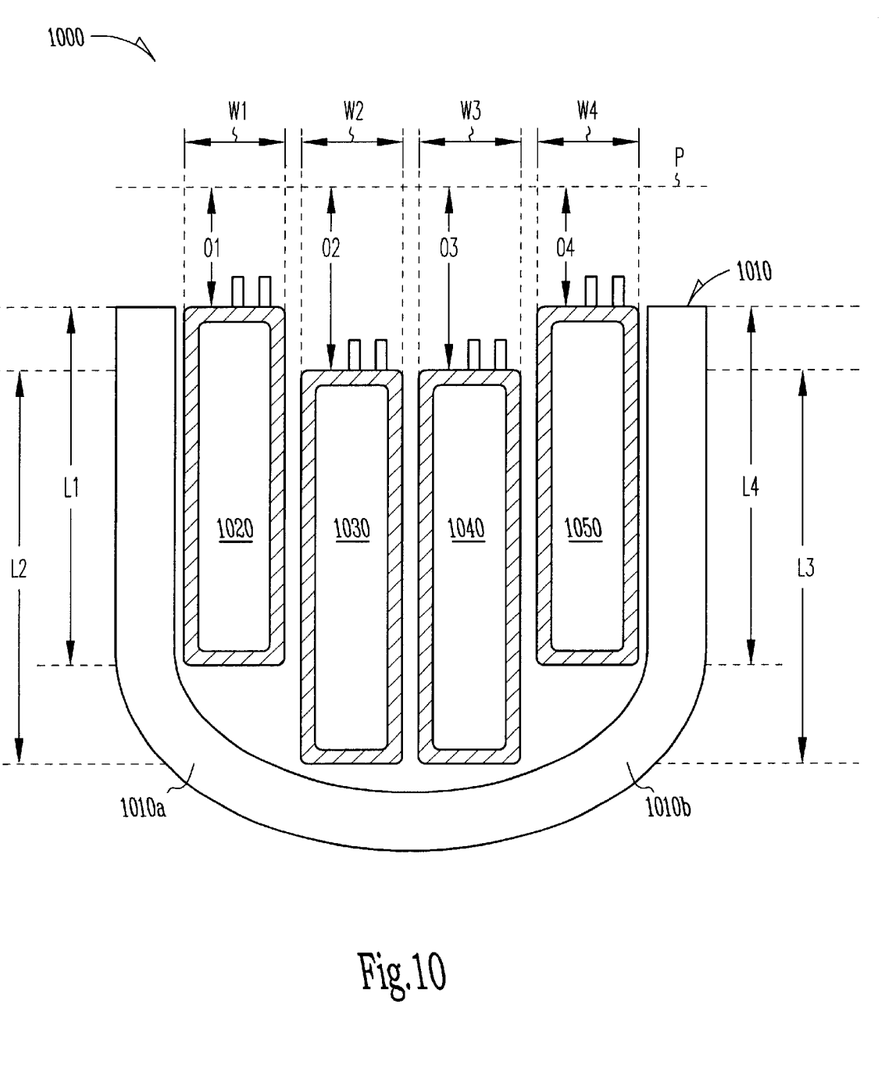
FIG. 10 is a partial cross-sectional view of an exemplary capacitor assembly 1000.

FIGS. 8, 9, and 10, all cross-sectional views, show respective four-capacitor assemblies, each illustrating a flexible capacitor-level approach to reducing the voids in implantable-device housings. In a mass-production context, the capacitor-level approach allows one to prefabricate a set of capacitors of different sizes, different curvatures, and even of different capacitor technologies, and then to assemble the capacitors to conform to the available space within a housing.

In particular, FIG. 8, a cross-sectional view, shows an exemplary capacitor assembly 800. Capacitor assembly 800 includes a monitor housing 810 and four separate capacitors 820, 830, 840, and 850. Housing 810 includes curved portions 810a, 810b, 810c, and 810d. Capacitors 820, 830, 840, and 850 include respective capacitor cases 822, 832, 842, and 852, and respective terminals pairs 824, 834, 844, and 854. (For clarity, the figure omits the internals of these capacitors.) Cases 822, 832, 842, and 852 have respective curved portions 822a, 832a, 842a, and 852a that are generally congruent to and confront respective curved portions 810a, 810b, 810c, and 810d of housing 810. The cases also have respective widths (or heights) W1, W2, W3, and W4 Each of capacitors terminal pairs 824, 834, 844, and 854 includes an anode terminal and a cathode terminal. Though not shown, the exemplary embodiment interconnects the terminals to achieve a series connection of two capacitances.

This exemplary embodiment provides the four capacitors with a common width. However, other embodiments provide one or more of the capacitors with a different width. For example, in some embodiments, widths W1 and W4 are equal, and widths W2 and W3 are equal, but different from widths W1 and W2. Additionally, two or more of the capacitors, for example, capacitors 820 and 830 or capacitors 820 and 830, can be combined into a single capacitor. And, still other embodiments use different numbers of capacitors, such as three, five, or six. Thus, the invention is not limited to an particular number of capacitors.

FIG. 9, a cross-sectional view, shows an exemplary capacitor assembly 900. Capacitor assembly 900 includes a monitor housing 910 and four separate capacitors 920, 930, 940, and 950. Housing 910 includes curved portions 910a and 910b. Capacitors 920, 930, 940, and 950 include respective capacitor cases 922, 932, 942, and 952, which have respective widths (or heights) W1, W2, W3, and W4, and respective lengths L1, L2, L3, and L4. Cases 922 and 932 have respective end walls 922a and 932a which confront curved portion 910a; and cases 942 and 952 have respective end walls that confront curved portion 910b.

In this exemplary embodiment, the capacitors lack individual curved profiles, but have different sizes to reduce voids between their respective cases and the monitor housing. More precisely, one or more of the capacitors has a different width and/or length. As shown, lengths L1 and L4 are equal to a length LA, and lengths L2 and L3 are equal to a different length LB. Also, widths W2 and W3 are equal to a width WA, and widths W1 and W4 are not equal to each other or to the width WA. However, in some embodiments, the capacitors have a common width.

FIG. 10, a cross-sectional view, shows an exemplary capacitor assembly 1000. Capacitor assembly 1000 includes a monitor housing 1010 and four separate capacitors 1020, 1030, 1040, and 1050. Housing 1010 includes curved portions 1010a and 1010b. Capacitors 1020, 1030, 1040, and 1050 include respective capacitor cases 1022, 1032, 1042, and 1052. Cases 1022, 1032, 1042, and 1052 have respective widths W1, W2, W3, and W4, and respective lengths L1, L2, L3, and L4. Additionally, cases 1022, 1032, 1042, and 1052 are offset from a common reference plane P by respective offsets O1, O2, O3, and O4.

In this exemplary embodiment, widths W1, W2, W3, and W4 are equal, and lengths L1, L2, L3, and L4 are equal. Further, offsets O1 and O4 are equal, and offsets O2 and O3 are equal but larger than offsets O1 and O4. In other embodiments, each of the offsets is larger than the previous offset, creating descending steps.

In the exemplary embodiments of FIGS. 8–10, the four capacitors are aluminum electrolytic capacitors, with each capacitor including one or more capacitor modules of similar or dissimilar structures (as previously described for other exemplary capacitors.) However, other embodiments provide the four capacitors as wet-tantalum, ceramic, dry-film capacitors, or other types of capacitors. Still other embodiments provide combinations of different numbers of capacitors and different types of capacitors.

Figure 11:
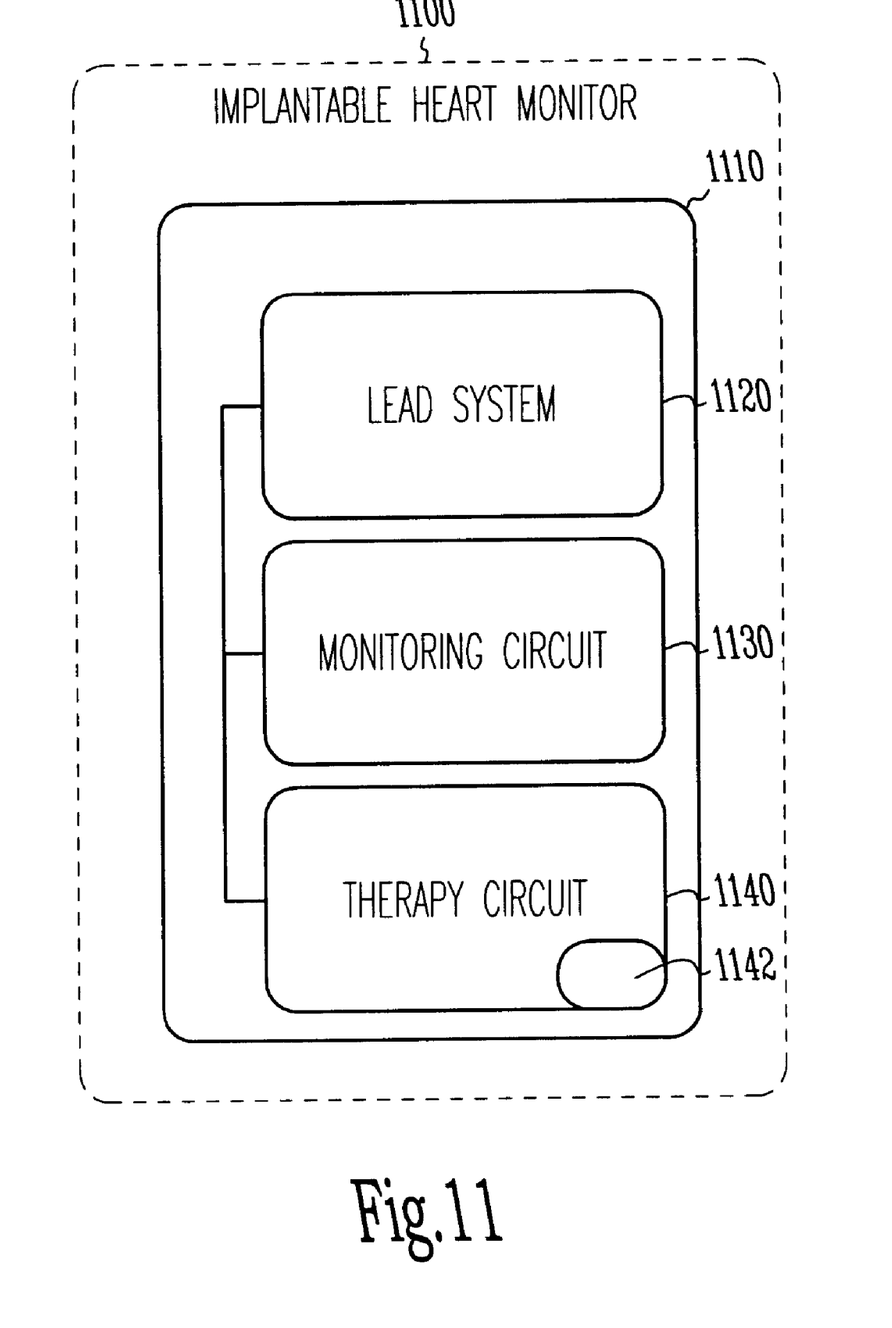
FIG. 11 is a block diagram of an implantable heart monitor 1100.

FIG. 11 is a block diagram of implantable heart monitor 1100 which incorporates one or more teachings of the present invention. Specifically, monitor 1100 includes a housing 1110, lead system 1120, which after implantation electrically contact strategic portions of a patient's heart, a monitoring circuit 1130 for monitoring heart activity through one or more of the leads of lead system 1120, and a therapy circuit 1140. Circuit 1140 includes a component 1142 which incorporates one or more capacitors, such as capacitors 100 and 300, capacitor-battery assembly 400, or one or more of capacitor assemblies 800, 900, or 1000. Monitor 1100 operates according to well known and understood principles to perform defibrillation, cardioversion, pacing, and/or other therapeutic functions.

In addition to its application to implantable heart monitors, or cardiac rhythm management devices, the teachings of the present invention are applicable to photographic flash equipment. Indeed, these teachings are pertinent to any application where small, high-energy capacitors are desirable.

CONCLUSION

In furtherance of the art, the present inventors have devised several new capacitor structures having curved profiles and capacitor assemblies for reducing voids in implantable medical devices. The curved profiles generally facilitate efficient use of curved capacitor cases and curved housings for implantable medical devices. In some exemplary embodiments, the capacitors include staggered capacitor modules or elements to define the curved profiles, and in other embodiments, the capacitors themselves are staggered.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A capacitor comprising:
   a case having a curved interior surface; and
   first, second, and third capacitor modules having respective first, second, and third edge faces that confront the curved interior surface of the case, with the third edge face set back from the second edge face and the second edge face set back from the first edge face to define a profile generally congruent to a profile of the curved interior surface.

2. The capacitor of claim 1, wherein the first and second capacitor modules each include an additional edge face that is not parallel to any of the first, second, and third edge faces, with the additional edge face of the first capacitor module set back from the additional edge face of the second capacitor module.

3. The capacitor of claim 1, wherein the case has a bottom and the first, second, and third capacitor modules are stacked in ordinal sequence from the bottom, with the first capacitor module closer to the bottom.

4. The flat capacitor of claim 1, wherein the first, second, and third capacitor modules have respective first, second, and third major surfaces having respective curved perimeter portions, with the first, second, and third edge faces corresponding to the curved perimeter portions.

5. An implantable medical device comprising the capacitor of claim 1.

6. The flat capacitor of claim 1, further including a fourth capacitor module having an anode and a cathode and having a fourth edge face that confronts the curved interior surface of the case and that is set back from the third edge face to further define the profile generally congruent to the profile of the curved interior surface.

7. The capacitor of claim 1, wherein each capacitor module comprises:
   two or more U-shaped aluminum foils; and
   at least one U-shaped dielectric layer between two of the aluminum foils.

8. The capacitor of claim 7, wherein the two or more U-shaped aluminum foils includes:
   at least first and second U-shaped foils that are electrically coupled to each other; and
   at least one U-shaped foil electrically isolated from the first and second U-shaped foils that are electrically coupled.

9. The capacitor of claim 8, wherein the one U-shaped dielectric layer lies between the one U-shaped foil and the U-shaped foils that are electrically coupled to each other.

10. The capacitor of claim 1:
    wherein the first capacitor module comprises:
       a first generally U-shaped capacitor module including:
          a first anode having two or more U-shaped conductive layers that are electrically coupled to each other; and
          a first cathode adjacent the first anode and having at least one U-shaped conductive layer; and
    wherein the second capacitor module comprises:
       a second generally U-shaped capacitor module stacked on the first generally U-shaped capacitor module, the second module including a second anode having two or more U-shaped conductive layers that are electrically coupled to each other and a second cathode having at least one U-shaped conductive layer.

11. An implantable medical device comprising the capacitor of claim 10.

12. The capacitor of claim 10, wherein each conductive layer comprises a metallic foil.

13. The capacitor of claim 10, wherein the first anode comprises a different number of U-shaped conductive layers than the second anode.

14. An implantable medical device comprising the capacitor of claim 13.

15. The capacitor of claim 10, wherein each module includes at least one U-shaped separator between its anode and its cathode.

16. The capacitor of claim 10, wherein the first and second U-shaped capacitor modules include respective first and second pairs of legs and respective first and second middle portions between the respective pairs of legs, with the second middle portion stacked on the first middle portion, and the first and second pairs of legs oriented in a common direction relative the first and second middle portions.

17. The capacitor of claim 16, wherein the first and second middle portions have respective first and second curved edge faces, with the second curved edge face offset from the second curved edge face.

18. An implantable medical device comprising the capacitor of claim 17.

19. The capacitor of claim 16, wherein each leg in the first and second pairs of legs has an edge face, with the edge face of one leg of the second pair of legs offset from the edge face of one leg of the first pair of legs, and with the one leg of the second pair of legs stacked atop the one leg of the first pair of legs.

20. An implantable medical device comprising the capacitor of claim 19.

21. An assembly for implantable medical devices, comprising:
    the capacitor of claim 10; and
    a medical-device component positioned within an open region at least partially enclosed by the generally U-shaped capacitor modules.

22. An implantable medical device comprising the assembly of claim 21.

23. The assembly of claim 21, wherein the medical-device component is a battery.

24. A capacitor comprising:

a case having a curved interior surface; and first, second, and third capacitor modules having respective first, second, and third pairs of nonparallel edge faces, with one edge face of each pair confronting the curved interior surface of the case, with the one edge face of the third pair of edge faces set back from the one edge face of the second pair of edge faces and the one edge face of the second pair of edge faces set back from the one edge face of the first pair of edge faces and with the other edge face of the first pair of edge faces set back from the other edge face of the second pair of edge faces.

25. The capacitor of claim 24, wherein the case has a bottom and the first, second, and third capacitor modules are stacked in ordinal sequence from the bottom, with the first capacitor module closer to the bottom than the second and third capacitor modules.

26. An implantable medical device comprising the capacitor of claim 24.

27. The capacitor of claim 24, wherein each capacitor module comprises:

a first foil having a first body region and at least one peninsular region extending from the first body region;

a second foil having a second body region and at least one peninsular region extending from the second body region; and a dielectric layer between the first and second foils.

* * * * *